United States Patent
Rector et al.

(10) Patent No.: US 9,174,355 B2
(45) Date of Patent: Nov. 3, 2015

(54) INCORPORATION OF METAL NANOPARTICLES INTO WOOD SUBSTRATE AND METHODS

(75) Inventors: Kirk D. Rector, Santa Cruz, NM (US); Marcel Lucas, Pullman, WA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 347 days.

(21) Appl. No.: 13/642,060

(22) PCT Filed: Apr. 20, 2011

(86) PCT No.: PCT/US2011/033284
§ 371 (c)(1),
(2), (4) Date: Dec. 19, 2012

(87) PCT Pub. No.: WO2011/133691
PCT Pub. Date: Oct. 27, 2011

(65) Prior Publication Data
US 2013/0199276 A1    Aug. 8, 2013

Related U.S. Application Data

(60) Provisional application No. 61/326,121, filed on Apr. 20, 2010.

(51) Int. Cl.
*B27K 3/00* (2006.01)
*G01N 33/46* (2006.01)
*B27K 3/02* (2006.01)
*B27K 3/16* (2006.01)
*B82Y 30/00* (2011.01)
*D21H 17/63* (2006.01)
*G01N 21/65* (2006.01)
*G01N 33/543* (2006.01)
*G01N 33/58* (2006.01)

(52) U.S. Cl.
CPC .............. *B27K 3/007* (2013.01); *G01N 33/46* (2013.01); *B27K 3/0221* (2013.01); *B27K 3/16* (2013.01); *B82Y 30/00* (2013.01); *D21H 17/63* (2013.01); *G01N 21/658* (2013.01); *G01N 33/54373* (2013.01); *G01N 33/587* (2013.01)

(58) Field of Classification Search
CPC ................................ B27K 3/007; G01N 33/46
See application file for complete search history.

(56) References Cited

U.S. PATENT DOCUMENTS

| 2003/0134137 A1 | 7/2003 | Laks et al. |
| 2005/0126338 A1* | 6/2005 | Yadav .................... B82Y 30/00 752/255 |
| 2008/0269186 A1 | 10/2008 | Bignozzi et al. |
| 2009/0084509 A1* | 4/2009 | Luo ........................... D01F 2/02 162/9 |
| 2009/0223408 A1 | 9/2009 | Richardson et al. |
| 2010/0065235 A1 | 3/2010 | Fike et al. |

OTHER PUBLICATIONS

Przybysz et al. "Ionic Liquids and Paper" Ind. Eng. Chem. Res. 2005, 44, 4599-4604.*
Banerjee et al., "Commercializing Lignocellulosic Bioethanol: Technology Bottlenecks and Possible Remedies," Biofuels, Bioprod. Biorefin., 2010, vol. 4, pp. 77-93.
Barneto et al., "Thermogravimetric measurement of amorphous cellulose content in flax fibre and flax pulp," Cellulose, 2011, vol. 18, pp. 17-31.
Bose et al., "Enzyme-Catalyzed Hydrolysis of Cellulose in Ionic Liquids: A Green Approach to the Production of Biofuels," J. Phys. Chem. B, 2010, vol. 114, pp. 8221-8227.
Buchelnikov et al., "Heating of metallic powders by microwaves: experiment and theory," J. Appl. Phys., 2008, vol. 104, pp. 113505-1 through 113505-10.
Datta et al., "Ionic liquid tolerant hyperthermophilic cellulases for biomass pretreatment and hydrolysis," Green Chem., 2010, vol. 12, pp. 338-345.
Demirbas et al., "Products from Lignocellulosic Materials via Degradation Processes," Energy Sources Part A, 2008, vol. 30, pp. 27-37.
Faix et al., "Study on low mass thermal degradation products of milled wood lignins by thermogravimetry-mass spectrometry," Wood Sci. Technol., 1988, vol. 22, pp. 323-334.
Fort et al., "Can ionic liquids dissolve wood? Processing and analysis of lignocellulosic materials with 1-n-butyl-3-methylimidazolium chloride," Green Chem. 2007, vol. 9, pp. 63-69.
Fox et al., "Flammability, thermal stability, and phase change characteristics of several trialkylimidazolium salts," Green Chem., 2003, vol. 5, pp. 724-727.
Fulkerson et al., "Comparison of the Thermal Conductivity, Electrical Resistivity, and Seeback Coefficient of a High-Purity Iron and an Armco Iron to 1000°C," J. Appl. Phys., 1966, vol. 37, No. 7, pp. 2639-2653.
Gabriel et al., "Dielectric parameters relevant to microwave dielectric heating," Chem. Soc. Rev., 1998, vol. 27, pp. 213-223.
Ge et al., "Thermal Conductivities of Ionic Liquids over the Temperature Range from 293K to 353K," J. Chem. Eng. Data, 2007, vol. 52, pp. 1819-1823.

(Continued)

*Primary Examiner* — Peter Macchiarolo
*Assistant Examiner* — Nathaniel Kolb
(74) *Attorney, Agent, or Firm* — Samuel L. Borkowsky; Bruce H. Cottrell

(57) ABSTRACT

Metal nanoparticles were incorporated into wood. Ionic liquids were used to expand the wood cell wall structure for nanoparticle incorporation into the cell wall structure. Nanoparticles of elemental gold or silver were found to be effective surface enhanced Raman spectroscopy (SERS) imaging contrast or sensing agents. Nanoparticles of elemental iron were found to be efficient microwave absorbers and caused localized heating for disrupting the integrity of the lignocellulosic matrix. Controls suggest that the localized heating around the iron nanoparticles reduces losses of cellulose in the form of water, volatiles and $CO_2$. The ionic liquid is needed during the incorporation process at room temperature. The use of small amounts of ionic liquid combined with the absence of an ionic liquid purification step and a lower energy and water use are expected to reduce costs in an up-scaled pretreatment process.

12 Claims, No Drawings

(56) References Cited

OTHER PUBLICATIONS

Huber et al., "Synthesis of Transportation Fuels from Biomass: Chemistry, Catalysts, and Engineering," Chem. Rev., 2006, vol. 106, No. 9, pp. 4044-4098.

Jones et al., "Molecular Analysis of Primary Vapor and Char Products during Stepwise Pyrolysis of Poplar Biomass," Energy & Fuels, 2010, vol. 24, pp. 5199-5209.

Kappe et al., "Controlled Microwave Heating in Modern Organic Synthesis," Angew. Chem. Int. Ed., 2004, vol. 43, pp. 6250-6284.

Kilpeläinen et al., "Dissolution of Wood in Ionic Liquids," J. Agric. Food Chem., 2007, vol. 55, pp. 9142-9148.

Kržan et al., "Microwave heating in wood liquefaction," J. Appl. Polym. Sci., 2006, vol. 101, pp. 1051-1056.

Lee et al., "Ionic liquid-mediated selective extraction of lignin from wood leaching to enhanced enzymatic cellulose hydrolysis," Biotechnol. Bioeng., 2009, vol. 102, pp. 1368-1376.

Liu et al., "Enhanced electromagnetic wave absorption properties of Fe Nanowires in gigahertz range," Appl. Phys. Lett., 2007, vol. 91, pp. 093101-1 through 093101-3.

Lucas et al., "Ionic Liquid Pretreatment of Poplar Wood at Room Temperature: Swelling and Incorporation of Nanoparticles," ACS Appl. Mater. Interfaces, 2010, vol. 2, No. 8, pp. 2198-2205.

Lucas et al., "Reversible swelling of the cell wall of poplar biomass by ionic liquid at room temperature," Bioresour. Technol., 2011, vol. 102, pp. 4518-4523.

Mészáros et al., "Thermogravimetric and Reaction Kinetic Analysis of Biomass Samples from an Energy Plantation," Energy & Fuels, 2004, vol. 18, pp. 497-507.

Pinkert et al., "Ionic Liquids and their Interaction with Cellulose," Chem. Rev., 2009, vol. 109, pp. 6712-6728.

Pottkämper et al., "Applying metagenomics for the identification of bacterial cellulases that are stable in ionic liquids," Green Chem., 2009, vol. 11, No. 7, pp. 957-965.

Robinson et al., "Microwave Pyrolysis of Wood Pellets," Ind. Eng. Chem. Res., 2010, vol. 49, pp. 459-463.

Shinde et al., "Investigation of structural, morphological, luminescent and thermal properties of combusted aluminum-based iron oxide," J. Solid State Chem., 2010, vol. 183, pp. 2886-2894.

Sims et al., "An Overview of Second Generation Biofuels Technology," Bioresour. Technol. 2010, vol. 101, pp. 1570-1580.

Singh et al, "Visualization of biomass solubilization and cellulose regeneration during ionic liquid pretreatment of switchgrass," Biotechnol. Bioeng., 2009, vol. 104, pp. 68-75.

Stark, A. "Ionic liquids in the biorefinery: a critical assessment of their potential," Energy Environ. Sci., 2011, vol. 4, pp. 19-32.

Suleiman et al., "Thermal conductivity and diffusivity of wood," Wood Sci. Technol., 1999, vol. 33, pp. 465-473.

Sun et al., "Complete dissolution and partial delignification of wood in the ionic liquid 1-ethyl-3-methylimidazolium acetate," Green Chem. 2009,11,646-655.

Swatloski et al., "Dissolution of Cellulose with Ionic Liquids," J. Am. Chem. Soc., 2002, vol. 124, pp. 4974-4975.

Van Valkenburg et al, "Thermochemistry of ionic liquid heat-transfer fluids," Thermochim. Acta, 2005, vol. 425, pp. 181-188.

Varhegyi et al., "Kinetics of the thermal decomposition of cellulose, hemicellulose, and sugarcane bagasse," Energy & Fuels, 1989, vol. 3, pp. 329-335.

Xie et al., "Thorough Chemical Modification of Wood-Based Lignocellulosic Materials in Ionic Liquids," Biomacromolecules, 2007, vol. 8, pp. 3740-3748.

Zakrzewska et al., "Ionic Liquid-Mediated Formation of 5-Hydroxymethylfurfural—A Promising Biomass-Derived Building Block," Chem. Rev. Jan. 2011, vol. 111, pp. 397-417.

Zavrel et al., "High-throughput screening for ionic liquids dissolving lignocellulose," Bioresour. Technol., 2009, vol. 100, pp. 2580-2587.

Zhang et al., "Microwave-assisted Conversion of Lignocellulosic Biomass into Furans in Ionic Liquid," Bioresour. Technol. 2010, vol. 101, pp. 1111-1114 (available online Oct. 1, 2009).

* cited by examiner

INCORPORATION OF METAL NANOPARTICLES INTO WOOD SUBSTRATE AND METHODS

RELATED APPLICATIONS

This application claims the benefit of U.S. Provisional Patent Application Ser. No. 61/326,121 entitled "Pretreated Wood Article and Method," filed Apr. 20, 2010, incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to incorporation of metal nanoparticles into wood substrates, to articles that are wood substrates with incorporated metal particles, to sensing changes in the chemical environment in such articles, and to treating such articles with microwaves.

BACKGROUND OF THE INVENTION

Lignocellulosic biomass is plant biomass that is composed of cellulose, hemicellulose, and lignin. Cellulose and hemicellulose are carbohydrate polymers that are tightly bound to the lignin. Lignocellulosic biomass can be grouped into four main categories: (1) agricultural residues; (2) energy crops; (3) wood residues, including sawmill and paper mill discards; and (4) municipal paper waste. Lignocellulosic biomass represents a potentially sustainable source of fuel and commodity chemicals, offers economic advantages over corn starch for the production of biofuels, and could contribute to carbon sequestration without impacting food crop prices [1]. Lignocellulosic biomass could satisfy the energy needs for transportation and electricity generation, while contributing to carbon sequestration and limiting the accumulation of greenhouse gases in the atmosphere.

Potential feedstocks of lignocellulosic biomass are abundant and include crops (e.g. corn and sugarcane), agricultural wastes, forest products (e.g. wood), grasses, and algae. Among the feedstocks, wood has been widely used for the production of paper, as a construction material, and as a solid fuel. Wood is composed mainly of cellulose, hemicellulose, and lignin. Lignin is an amorphous network of crosslinked phenylpropanoid units.

The conversion of lignocellulosic biomass into liquid fuels and/or other commodity chemicals typically includes the following steps: (1) pretreatment; (2) hydrolysis of cellulose and hemicellulose into fermentable sugars; and (3) fermentation of the sugars into the liquid fuels (e.g. ethanol) and other commodity chemicals. The pretreatment is energy-intensive, but necessary due to the complex structure of the plant cell wall and the chemical resistance of lignin, which limits the access of enzymes to cellulose. An ideal pretreatment should break the lignocellulosic complex, increase the active surface area, and decrease the cellulosic crystallinity while limiting the generation of inhibitory by-products and minimizing hazardous wastes and wastewater.

A major bottleneck in the large-scale conversion of biomass to biofuels is the pretreatment delignification process that provides enzymes access to cellulose, the main source of fermentable sugars. Most current pretreatments, such as ammonia fiber explosion, alkaline hydrolysis, and acid hydrolysis, require high temperatures that increase the operation costs and generate toxic byproducts [2, 3]. The pretreatment is also the most expensive step in the conversion of lignocellulosic biomass to ethanol. Less expensive pretreatments that are environmentally friendly are desirable.

Ionic liquids are molten salts with melting points at or below a temperature of 100° C. They are characterized by their high conductivity, high density, high thermal conductivity, high thermal stability, and extremely low vapor pressure. Alternative pretreatments involving ionic liquids have been investigated because ionic liquids can dissolve in a few hours various native biomasses that include corn stalk [4, 5], rice straw [4, 5], pine [4, 5, 6, 7, 8], oak [6, 7], spruce [8, 9, 10], maple [11], switchgrass [12], and poplar [7]. At elevated temperatures, typically above 90° C., ionic liquids can dissolve cellulose, lignin, native switchgrass, and wood sawdust ground from spruce, pine, and oak. Furthermore, ionic liquids can be recycled at high yields for further use. Most of these reported studies in ionic liquids were conducted at high temperatures on a conventional heating plate. In a typical recycling process, cellulose-rich wood extracts are precipitated and filtered out. The lignin and other extracts are removed with multiple washings and solvent evaporation. Regenerated cellulose from an ionic liquid solution of wood may have a lower degree of polymerization and crystallinity, which facilitates its hydrolysis. A few microbial celluloses remain active at an ionic liquid concentration of about 30%.

The great potential of ionic liquids is due to their low vapor pressure, thermal stability and flexibility because many anion-cation combinations are possible. A few celluloses can tolerate high concentrations of ionic liquids [13, 14, 15].

Microwave irradiation has been increasingly used in chemistry to reduce reaction times from several hours to less than a minute in some cases [16]. It was also applied to the pyrolysis of pine wood pellets [17]. Most studies were conducted in commercial microwave ovens [4, 6, 18], with a few in microwave cavities [17] at a frequency of 2.45 GHz. In contrast to conventional heating plates that rely on conduction and convection, microwave irradiation offers several advantages, including volumetric heating and quick coupling with molecules in the sample, that lead to enhanced energy efficiency [17]. It heats materials through two main mechanisms: dielectric loss in dipolar polarization and friction during ionic conduction [16].

Dry wood has a low dielectric loss factor at temperatures up to 500° C., making it a poor microwave absorber [17]. The addition of water, a strong microwave absorber at 2.45 GHz, to wood improves the conversion of microwaves into heat [17].

Microwaves have been recently used to accelerate the dissolution of wood in ionic liquids [4, 6, 18] and acids [19] with pulses as short as a few seconds. Ionic liquids are excellent microwave absorbers because they are polar and ionic in nature [16, 20]. The use of microwave pretreatment (60×3 s pulses) before conventional heating reduced the time it takes to completely dissolve pine sawdust in 1-ethyl-3-methylimidazolium acetate (EMIMAc) by a factor of about three [6], in another study, microwave irradiation increased significantly the yield of 5-hydroxymethylfurfural and furfural produced from the dissolution of pine wood in 1-butyl-3-methylimidazole chloride, while reducing the reaction time from 60 mM (conventional heating with oil bath at 100° C.) to 3 min [4]. In these studies, the biomass was completely immersed in ionic liquid and the dissolution products had to be separated from the ionic liquid, which requires additional energy and water use. Also, due to the high cost of ionic liquids, their recycling is essential for the economic viability of an up-scaled process [21].

SUMMARY OF THE INVENTION

The present invention includes a wood article comprising wood and nanoparticles incorporated into cell walls in the wood, wherein the nanoparticles comprise an elemental metal.

The present invention also includes a method for studying wood. The method involves exposing a wood substrate having cell walls to an ionic liquid that is a molten salt that has a melting temperature at or below a temperature of 100° C. to induce swelling in the wood, then exposing the swollen wood to an aqueous suspension of nanoparticles, the nanoparticles having surfaces, whereby at least some of the nanoparticles become incorporated into the cell walls, whereby the nanoparticles comprise an elemental metal or metal oxide, and thereafter performing a technique on the wood substrate with nanoparticles incorporated therein selected from surface enhanced Raman microscopy and surface enhanced Raman spectroscopy, wherein said nanoparticles behave a contrast agent for studying the wood.

The present invention also includes a sensor capable of responding to changes in the concentration of an analyte in a wood substrate, comprising: a wood substrate comprising cell nanoparticles deposited in the cell walls in the wood substrate, wherein the nanoparticles comprise a metal selected from gold, silver, and copper, said nanoparticles further comprising surfaces, and ligands attached to the surfaces of the nanoparticles, wherein the nanoparticles with attached ligands are capable of responding to changes in the concentration of an analyte in the wood substrate. When nanoparticles are not attached with ligands they sense the presence of chemicals in the wood (e.g. cellulose or lignin). When nanoparticles are attached with ligands (for example 4-mercaptopyridine), they sense the ligands and how the ligands respond to the chemical environment (e.g. to changes in the concentration of various analytes including but not limited to hydrogen ions, metal ions, gases, liquids, and the like). The wood can then be subjective to a pretreatment or mechanistic study utilizing the modified wood as the substrate.

The invention also includes a method for post-harvest modification of wood or cellulose-based paper, comprising: providing a substrate having a structure that comprises cell walls, the substrate being selected from wood and cellulose-based paper, and incorporating isotopically-enriched cellulose crystals into the cell wall structure.

The present invention also includes a method for studying wood, comprising: providing a substrate having a structure that comprises cell walls, the substrate being selected from wood and cellulose-based paper, incorporating isotopically-enriched cellulose crystals into the cell wall structure, and subjecting the wood to a pretreatment or mechanistic study utilizing the isotopically-enriched cellulose crystals inside the wood substrate.

The present invention also includes a method for treating wood. The method includes exposing wood having cell walls to an ionic liquid that is a molten salt that has a melting temperature at or below a temperature of 100° C. to induce swelling in the wood, and thereafter exposing the now swollen wood to an aqueous suspension of nanoparticles whereby at least some of the nanoparticles become deposited into cell walls, wherein the nanoparticles comprise an elemental metal, and thereafter subjecting the wood and metal nanoparticles inside the wood to microwaves.

DETAILED DESCRIPTION

All numerical amounts are understood to be modified by the word "about" unless otherwise specifically indicated.

All documents cited herein are incorporated herein by reference. The citation of any document is not to be construed as an admission that it is prior art with respect to the present invention.

To the extent that any meaning or definition of a term in this document conflicts with any meaning or definition of the same term in a document incorporated by reference, the meaning or definition assigned to that term in this document shall govern.

The present invention is concerned with an article of pretreated wood containing metal nanoparticles deposited into cell walls in the wood. The invention is also concerned with a method of pretreating the wood. The pretreatment involves incorporating metal nanoparticles in the wood. The pretreatment involves swelling the wood using an ionic liquid. The ionic liquid is a molten salt having a melting temperature equal to or below 100° C.

The method of this invention may be applied to any kind of wood or paper products. Poplar was selected merely to show how the method may be performed. Any other type of wood may be used instead of poplar. For example, a non-limiting list of wood that may be used includes cedar, pine, mahogany, oak, cherry, ash, maple, birch, teak, cocobolo, walnut, rosewood, hickory, rubberwood, lyptus, alder, basswood, koa, korina, spruce, lacewood, fir, and the like. The method of the invention can also be applied to the treatment of other feedstocks such as corn stovers, rice straw, wheat straw, switchgrass and municipal paper waste. The method of the invention can also be applied to the treatment of wood-based products such as paper, construction materials, and cardboard.

Briefly, the ionic liquid exposure caused the wood to swell. Subsequent exposure to a metal nanoparticle suspension resulted in diffusion of metal particles into the cell walls in the wood, and then contraction of the wood, which trapped the metal particles in the cell walls. Many of the nanoparticles remained inside the wood after rinsing. Incorporation occurs after exposing the wood sample to ionic liquid for a period of time less than 1 hour. Control experiments on untreated wood samples did not allow the wood to swell, limiting deposition of nanoparticles only at the surface and most of them were removed by rinsing the samples.

Transverse sections of poplar wood (*Populus tremuloides*) ranging from 30-50 μm thickness were cut with a sliding microtome. The sections were dried in an oven for 4 hours between glass slides at 60° C. to prevent curling. The poplar sections were then cut into rectangular pieces of typical dimensions 3×4 mm$^2$. Sawdust (30 mesh) was also ground from poplar blocks. The ionic liquid 1-ethyl-3-methylimidazolium acetate (EMIMAc), ferric oxide ($Fe_2O_3$) and magnetite ($Fe_3O_4$) nanopowder (<50 nm diameter) were purchased from Sigma-Aldrich (St. Louis, Mo.) Iron (average particle size 10-30 nm) and copper (20-40 nm) nanopowder were purchased from Alfa Aesar (Ward Hill, Mass.). Suspensions of 20 nm silver, 60 nm silver, 40 nm gold, and 100 nm gold nanoparticles were purchased from BBInternational, Cardiff, United Kingdom.

The method of the invention may so be used with an ionic liquid other than 1-ethyl-3-methyl-imidazolium acetate that is also a molten salt with a melting temperature at or below 100° C. 1-ethyl-3-methyl-imidazolium cation may be combined with other counter ions besides acetate to provide an ionic liquid useful with this invention. Some of these include, but are not limited to, chloride, fluoride, bromide, iodide, nitrate, sulfate, sulfonate, fluoalkylsulfonate, perchlorate, phosphate, silicate, and the like. A non-exhaustive list of ionic liquids, at least some of which are molten salts at a temperature of or below 100° C. is provided by Hagiwara et al. in "Room Temperature Ionic Liquids of Alkylimidazolium Cations and Fluoroanions", J. Fluorine Chem, vol. 105, (2000), pp. 221-227, incorporated by reference herein. Those ionic liquids failing within the guidelines of molten salts having a melting temperature at or below 100° C. can be used with this invention. PCT Patent Application WO 01/93363 to McEwen et al. entitled "Non-Flammable Electrolytes", also incorporated by reference, also provides a variety of ionic liquids that may be used with this invention. Those from McEwen et al. that are molten salts having a melting temperature at or below 100° C. may be used with this invention. Some preferred organic cations of molten salts useful with the invention include, but are not limited to, pyridinium, pyridazinium, pyrimidinium, pyrazinium, imidazolium, pyrazolium, thiazolium, oxazolium, and triazolium. Also included are alkyl-substituted analogs of these materials. A preferred list of quaternary ammonium based ionic liquids are those with a melting temperature at or below 100° C. that appear in Table I of the publication by Sun et al. entitled "Room-Temperature Molten Salts Based on the Quaternary Ammonium Ion," J. Phys. Chem. B, 1998, vol. 102, pages 8858-8864, incorporated by reference herein, and in U.S. Pat. No. 5,827,602 to Koch et al. entitled "Hydrophobic Ionic Liquids," which issued Oct. 27, 1998, also incorporated by reference herein.

The invention is also concerned with a method for pretreatment of wood. In an embodiment, samples of thin sections of poplar wood were immersed in ionic liquid at room temperature. This exposure caused the samples of wood to swell. Each of the swollen samples was then exposed to an aqueous suspension of metal nanoparticles. The swelling facilitated introduction of the metal nanoparticles into the wood, but exposure to the suspension also resulted in contraction, trapping metal nanoparticles in the cell walls inside the wood. In various embodiments, silver nanoparticles and gold particles were incorporated into the wood. These metal particles ranged in size from 20-100 nanometers (nm). Other elemental metals besides gold and silver were used. For example, nanoparticles of elemental iron were also used. Metal oxides nanoparticles were also used. For example, iron oxide nanoparticles were also used.

Poplar wood sections immersed in 1-ethyl-3-imidazolium acetate were examined by fluorescence microscopy using a ZEISS LSM 510 confocal system mounted on a ZEISS AXIOVERT 200M inverted microscope. A 514 nm laser was used as excitation and the fluorescence signal was collected with the Meta detector over a 600-620 nm range with a 63x oil objective (NA 1.4). After a 3-hour immersion, the cell walls became swollen and the cell lumens were reduced (similar behavior has been observed with switchgrass). From cross-sectional area measurements of poplar wood cells, it was found that after the 3 hour pretreatment, the cell wall areas increased by 60% to 100% and the lumen areas were reduced by 40% to 83%, depending on the original cell size in the dry wood. Afterward, a gentle rinsing with deionized water led to the almost immediate reopening of the lumen. The cell walls also contracted after rinsing with water, but more slowly. By contrast, the deposition of deionized water droplets on untreated poplar wood resulted only in a limited expansion of the wood, and the wood cells recovered their original sizes within 30 minutes after the water evaporated.

The expansion of the wood cells as a result of immersion in the ionic liquid, and subsequent contraction resulting from exposure to the suspension of metal nanoparticles, followed by rinsing with water, is basis of a process to incorporate nanoparticles, and potentially other material and chemicals into the wood structure. To this effect, the water rinsing is replaced by the exposure of the ionic liquid pretreated sample to an aqueous suspension of nanoparticles.

Nanoparticles of any suitable metal may be used. Nanoparticles of transition metals may be used. Nanoparticles of alkaline earth metals may be used. Nanoparticles of main group metals may be used. Nanoparticles of iron, tin, cobalt, titanium, niobium, tantalum, chromium, molybdenum, tungsten, nickel, copper, and the like, including mixtures and alloys of these materials, may be used. A preferred embodiment involves nanoparticles of elemental gold or silver to serve and contrast and sensing agents in wood. Another preferred embodiment involves nanoparticles of elemental iron, in particular when microwaves are used with iron nanoparticle-incorporated wood.

Nanoparticles have a high surface-to-volume ratio and may be chemically functionalized. Some potential applications of the method, which involves swelling of the wood using the ionic liquid, include isotope tracing, catalysis, imaging agents, drug-delivery systems, energy storage devices, and chemical sensors.

Penetration of metal (e.g. gold) nanoparticles of 100 nm diameter in the cell walls was confirmed by near-infrared confocal Raman microscopy. Raman spectroscopy has provided information related to spatial distribution of lignin and cellulose in cell walls, phase transition in cellulose, chemical modification, orientation of the molecules, and mechanical stress.

It is believed that the incorporation of material is stochastic in nature and the incorporation of material may be due to an affinity of the material to the substrate and the size of the cell wall structures, which typically are 2-3 micrometers in thickness, and thus the interface between two cell walls is 4-10 micrometers. Thus materials with sizes less than 2 micrometers are potentially able to be incorporated into cell walls, and possible bigger materials with sizes less than 50 micrometers may be incorporated into paper. Any elemental materials, charged or neutral and in any oxidation state, in this size range, as well as inorganic oxide, sulfides, or halide-based materials, may be incorporated into the cell walls. Organic-based materials, such as polymers, proteins, and nucleic acid based if they are small enough to enter the cell walls by diffusion. The incorporation of ceramic based phosphors could be used for advanced display technology.

The incorporation of gold nanoparticles into wood induces a significant enhancement in the Raman signal from the wood. This enhancement is believed to be due to a surface-enhanced Raman signal (SERS) effect.

The incorporation of materials into wood or paper products may provide nanoparticle-based sensors useful for measurement of chemical environment, for the presence of specific materials, for quantification of an amount of a chemical present, and the like. Both liquid-based detection and gaseous based detection using metal nanoparticles could be adapted to be incorporated into wood or paper using this invention. For liquid-based chemical sensing, specifically targeted SERS-based nanosensors, see for example U.S. Nonprovisional application Ser. No. 12/534,612 to Rector et al. entitled "Surface-enhanced Raman Scattering (SERS) Based Nanoparticle Composites," incorporated by reference, with both a sensing and targeting function for live cellular analyses. Other Ag, Au and Cu based nanoparticles use changes in the surface plasmon resonance for detection of the binding of an analytic. For fluid based detection, see also U.S. Pat. No. 6,773,926: "Nanoparticle-based Sensors for Detecting Analytes in Fluids," incorporated by reference. For gaseous samples, Au-nanoparticles can be proficiently employed as gate material in Si-Field Effect Gas Sensors. Preliminary results show interesting selectivity and sensitivity sensing features towards $NO_x$ detection (demonstrated in "Gold Nanoparticle Sensors For Environmental Pollutant Monitoring," Ieva et al., Proceedings of the 2007 2nd IEEE international Workshop on Advances in Sensors and interfaces 30-3 2007, incorporated by reference). Use of palladium nanoparticles can be used to sense gaseous $H_2$. Properties of paper which may improve upon existing sensing technology include, low cost, organic-based liquid and gas permeable, and thermally and electrically isolating.

Diffraction techniques and high-resolution solid-state $^{13}C$ NMR spectroscopy have been employed as powerful tools to gain a deeper insight into the crystal structures of the cellulose polymorphs as well as understanding of the chemical and biochemical deconstruction of lignocellulosic biomass. Frequently, it is desirable to using isotopic enrichment (such as $^{13}C$ labeling) to spectrally separate C-based materials from the biomass or from the chemical or biochemical treatment. One path is to provide isotopically enriched substances to grown poplar materials, for example as described in "Contribution of Different Carbon Sources to Isoprene Biosynthesis in Poplar Leaves" Schnitzler et al. Plant Physiology 135:152-160 (2004), incorporated by reference, which can be labor intensive or impractical. Alternatively it has been shown that $^{13}C$-enriched crystalline cellulose derivatives can be biosynthesized from D-(2-$^{13}C$) glucose, D-(3-$^{13}C$)glucose, or D-(5-$^{13}C$)glucose as a carbon source by $A.$ $xylinum$ as described in "CPRVIAS 13C NMR Study of Cellulose and Cellulose Derivatives, 2. Complete Assignment of the $^{13}C$ Resonance for the Ring Carbons of Cellulose Triacetate Polymorphs" Kono et al, J. Am. Chem. Soc., 2002, 124 (25), 7512-7518, incorporated by reference. Here is described a method for the post-harvest modification of wood or cellulose-based paper to incorporate these isotopically-enriched cellulose crystals into the cell wall structure which may not have otherwise negative effects on the cell wall structure. In an embodiment of the present invention, the swelling of poplar substrates, and then treatment by isotopically-enriched ($^{13}C$-enriched, $^2H$ enriched, for example) aqueous cellulose crystals, should trap the crystallites into the cell wall structure, thus enriching the overall sample. These isotopically enriched samples can then be subjected to all of various pretreatment or mechanistic studies where the source of the isotopic enrichment is known to be from the wood substrate.

The excitation for the Raman work was the 776 nm laser line of a tunable Ti:Sapphire laser (MIRA 900-P, COHERENT, Palo Alto, Calif.) coupled with a 532 solid state laser (MILLENIA VIIIs, SPECTRA-PHYSICS, Mountain View, Calif.). The incident laser was filtered spectrally by a short-pass filter at 785 nm (RAZOREDGE SP01-785RU-25, SEMROCK, Rochester, N.Y.). The collimated beam was focused to a line using a plano-convex BK 7 150-millimeter focal length cylindrical lens (CKX150AR.16, NEWPORT CORP., Irvine, Calif.) and was then redirected to the back of an inverted microscope (CARL ZEISS AXIOVERT 200, Gottingen, Germany) by a Raman edge dichroic (z785rdc, CHROMA TECHNOLOGY, Rockingham, N.Y.). Spatial coordinates with a submicron accuracy from the microscope stage (MS2000XY stage, APPLIED SCIENTIFIC INSTRUMENTATION INC., Eugene, Oreg.) and bright field images at different magnifications from an INFINITY X-32 camera (LUMENERA CORP., Ottawa, Canada) ensured the accurate registry required for the capture of Raman and SEM images at the same area after any sample preparation step. A C-apochromat 63x (N.A. 1.2) water immersion objective (CARL ZEISS) focused the laser line to a line approximately 1 micrometer wide and 100 micrometers long on the sample, with a total power of 80 milliwatts (mW) at the sample.

The Raman signal was collected in a backscattering configuration through the same objective and dichroic. The signal was focused with a 150 mm spherical lens onto a 50 micrometer wide slit at the entrance of a HOLOSPEC f/2.2 spectrograph (KAISER OPTICAL SYSTEMS Ann Arbor, Mich.) and filtered with a HOLOGRAPHIC SUPERNOTCH-PLUS filter (HSPF-785.0 AR-2.0, KAISER OPTICAL SYSTEMS, Ann Arbor, Mich.). The signal was then dispersed with a holographic grating (HSG-785-LF, KAISER) and imaged with a liquid nitrogen-cooled CCD camera (LN/CCD-1024E, PRINCETON INSTRUMENTS, Trenton, N.J.). The CCD camera recorded spectral information along the horizontal direction and spatial information along the vertical direction. The spectrometer was calibrated spectrally with 4-acetamidophenol, and spatially using lines in the $7^{th}$ group of a USAF-1951 resolution test target. Custom-written LABVIEW code (NATIONAL INSTRUMENTS, Austin, Tex.) enabled the acquisition of images and their correction for CCD bias voltage, spherical aberrations using the lines of a Kr lamp (NEWPORT CORP, Irvine, Calif.), and for the non-uniform power along the focused laser line using a NIST relative Raman intensity correction standard (MST SRM 2241). The Raman images were acquired by moving the sample across the laser line by 0.5 micrometer steps. The exposure time for each line was two minutes.

For the collection of Raman images at different depths, an additional pinhole was added before the spectrograph to reduce out-of-focus signals from the sample. The pinhole aperture diameter was decreased to reduce the Raman signal by a factor of 10. Since the signal is focused on a slit at the entrance of the spectrograph, the spatial resolution remains higher along the horizontal direction of the CCD camera than along the vertical direction. The objective was moved along the depth direction by 2 micrometer steps. The exposure time for the Raman images at different depths was 30 seconds for each line.

The data analysis was performed using custom-written LABVIEW code. Each CCD image corresponds to the signal from a line on the sample, and consists of 256 spectra collected at regular spatial intervals along that line. Each spectrum was integrated from $1050\,cm^{-1}$ to $1140\,cm^{-1}$ to form one line of the resulting Raman image. Apart from the CCD bias voltage, no other background from the sample was removed from the data. For the Raman intensity depth profile of hot spots, the intensity of all pixels in a 2×2 micrometer squared area (total of 32 pixels) around each spot was integrated for each image at a particular depth (hot spots in surface enhanced Raman scattering experiments refers to significantly higher than average enhancement of the Raman signal intensity, and is usually believed to arise from specific atomic and nanometer level structures on the surface or from multiple surfaces such as particles aggregating together). To normalize the intensity depth profile of each spot, its minimum value was subtracted from it and it was then divided by its maximum value. The error bars represent the uncertainty on the position of the selected 2×2 micrometer squared area around the hot spot.

In various embodiments of the invention, samples of wood were treated first with ionic liquid and then with a suspension of metal nanoparticles. After rinsing with water, images of the wood were obtained using scanning electron microscopy (SEM) and Raman spectroscopy to examine the effects of rinsing on the removal of nanoparticles from the wood. The images were of the same areas of the wood. Scanning electron micrographs were acquired using a FEI QUANTA 200FEG operating at an accelerating voltage of 30 kV with a backscatter detector. Samples were mounted on one of the glass cover slips used during Raman imaging. The images show that the step of rinsing was not very effective at removing nanoparticles that were deposited in the cell walls of the wood. It is believed that rinsing was not effective because exposure to the aqueous suspension of nanoparticles also resulted in a contraction of the wood, which trapped the nanoparticles into the cell walls. Most of the nanoparticles that deposited inside the wood remained inside the wood after rinsing.

Raman images were obtained at different depths in the wood to examine the depth of penetration of the nanoparticles inside the wood. These images revealed that a significant number of nanoparticles were incorporated into the wood sample at depths up to at least 4 micrometers. For metal nanoparticles having a diameter of approximately 100 nanometers, depth of 4 micrometers represents about 40 times the diameter of the nanoparticles.

Control experiments were also performed on samples of poplar wood. The control experiments did not involve exposure of the wood to the ionic liquid. Without this exposure, the swelling of the wood from water was greatly less. When these samples were then exposed to the aqueous suspension of metal nanoparticles, the result was that nanoparticles deposited only on the outer surface of the wood. These nanoparticles were easily removed by rinsing.

The majority of nanoparticle incorporation occurs after exposing the wood to ionic liquid for a period of time less than 1 hour. It is believed that the swelling resulting from ionic liquid exposure produces a disruption of a hydrogen bond network in the wood, which provides metallic nanoparticles access to the wood structure To examine the effects of the ionic liquid, two poplar wood samples having dimensions of approximately 5×5 mm$^2$ were cut from the same microtome section of 30 micrometers in thickness. One of the wood samples was immersed in 1-ethyl-3-methylimidazolium acetate for 3 hours at room temperature. After the immersion, excess ionic liquid was blotted from the wood using a KIMWIPE. The samples were placed on glass cover slips and 5 milliliters of a suspension of gold nanoparticles were placed on the samples. After applying the suspension of gold nanoparticles, the samples were left overnight in the air. The next day, they were then placed between glass cover slips for Raman imaging and then were rinsed with deionized water and left to dry overnight in the air, and afterward they were placed between new cover slips for further examination.

In an embodiment, rectangular samples of poplar wood were cut from 40 micrometer thick microtome sections. These samples were immersed in 1-ethyl-3-methyl imidazolium acetate. Afterward, they were exposed to a suspension of 20 nm silver nanoparticles for various amounts of time, and then rinsed with water and then placed in between glass slides and dried in an oven for 4 hours at 60° C., and then cooled. After cooling, their uptake of silver nanoparticles was examined.

An EDAX EAGLE 111 energy dispersive X-ray fluorescence (XRF) microscope was used to quantify nanoparticle uptake by averaging fluorescence over areas of diameter 40-160 micrometers. The instrument includes a rhodium (Rh) source. Settings of 40 kV accelerating voltage, 800 microamperes current, and 50 microseconds dwell time were used to sample the poplar wood sections. In this configuration, only elements with atomic numbers greater than 11 (Na) are detected. In a typical poplar spectrum, several elements are present including S, K, Ca, P, and Mn. The presence of elements S, K. Ca, P, and Mn has been reported in Aspen ash. The calcium content was heterogeneous. The signal from phosphorus was weak, but detectable. There was also some in situ Si content with likely contamination arising from pressing the poplar sections between glass slides during drying. In addition, Cr, Fe, Ni, Cu were detected, likely present as residue particulates from the microtome blade, in a comparison of total count mapping and elemental mapping, it was determined that K, Mn, and S are the most closely related to both the density and mass of the poplar sample and appear to be homogeneous with material thickness or density. Sulfur concentration (230 keV) was selected as an indicator of poplar density as it is most isolated from other spectral signatures. The determination of S and Ag (22.1 keV) concentrations was performed using a corrective baseline average algorithm. The only additional element detected after introduction of 1-ethyl-3-methylimidazolium acetate in the poplar samples was bromine, which was removed after rinsing with water.

As the incorporation of silver or gold nanoparticles into the poplar substrate is inhomogeneous even at the 100 micrometer distance scale, microscopic analyses alone are insufficient to quantify nanoparticle uptake. Therefore, XRF microspectroscopy was employed to quantify and to test experimental conditions to maximize uptake. The exposure time to ionic liquid was varied (up to 4 hours) followed by separate, fixed exposure to a suspension of silver nanoparticles (1 or 4 hours). TABLE 1 below, to an error within 10%, reports incorporation of 20 nm Ag nanoparticles into thin substrates of poplar wood as a function of ionic liquid exposure time from 0-4 hours and after exposure to the suspension of Ag nanoparticles.

TABLE 1

| Ionic liquid | Ag time (hours) | Ag/S K ratio |
| --- | --- | --- |
| 0 | 1 | 0.0016 |
| 1 | 1 | 0.02 |
| 2 | 1 | 0.22 |
| 0 | 4 | 0.0052 |
| 2 | 4 | 0.19 |
| 4 | 4 | 0.32 |

As a negative control, the poplar sample was exposed to the silver suspension for one or four hours without the ionic liquid pretreatment, and rinsed to test for the possibility of silver mechanical or electrostatic association. The XRF measurements indicated that silver was present in the control samples at the detection limit of the instrument. Slightly more silver was present when the wood was exposed for a longer time. In all experiments, exposure to both the ionic liquid and the silver suspension resulted in at least an order of magnitude increase in the particle incorporation. The data suggest that exposure to the ionic liquid or silver suspension longer than 1 hour has only a minor influence on particle incorporation. Further, increased exposure to silver has a negligible or minor influence on particle incorporation on these timescales.

According to an embodiment method of this invention, it was possible to incorporate materials into wood or paper for imaging or sensing applications. For the microscopy experiments, thin sections of poplar were pretreated for 3 hours with 1-ethyl-3-methyl-imidazolium acetate and then exposed to a suspension of 100 nm gold nanoparticles. In a control experiment, an untreated poplar wood section was also exposed to the same suspension of nanoparticles. After the deposition of the nanoparticles, Raman images were collected at different areas from the untreated sample and the one treated with the ionic liquid. In addition to the cellulose Raman signal which revealed the wood cell walls, there were multiple hot spots attributed to the presence of gold nanoparticles or aggregates of nanoparticles. The Raman signal at these hot spots is significantly enhanced due to the field enhancement in close proximity of gold nanoparticles. The enhancement, which reaches two orders of magnitude for some hot spots, indicates that the laser excitation energy is close to the surface plasmon resonance of these nanoparticles of 100 nm diameter, or clusters of these nanoparticles. Using the same excitation, no noticeable enhancement was observed from 20 nm diameter silver nanoparticles deposited on wood, while only a small enhancement was observed for 60 nm silver and 40 nm gold nanoparticles. Therefore, only the 100 nm gold nanoparticles will be dealt with in the following discussion. Raman images were obtained by integrating Raman spectra from $1050$ $cm^{-1}$ to $1140$ $cm^{-1}$, a band that includes the cellulose peaks typically located at approximately $1.095$ $cm^{-1}$ and $1120$ $cm^{-1}$ in spontaneous Raman spectra (not enhanced by gold nanoparticles). These two cellulose bands are enhanced by a variable factor depending on the hot spot. Also, the $1095$ $cm^{-1}$ band can be shifted to another position from $1081$ $cm^{-1}$ to $1099$ $cm^{-1}$, while the position of the $1120$ $cm^{-1}$ band varies from $1115$ $cm^{-1}$ to $1128$ $cm^{-1}$. The lignin peak at approximately $1600$ $cm^{-1}$ was not integrated because it overlapped with background signals from the ionic liquid and the glass substrate. Raman images show that the density of hot spots on the untreated sample is comparable to the one on the pretreated sample. The intensity of the hot spots was higher on the pretreated sample. This is partially explained by an overlap between the cellulose and the ionic liquid Raman bands.

After examining the samples by Raman spectroscopy, they were rinsed with deionized water at similar flow rates and left to dry overnight in air. A second series of Raman images at the same areas were collected after rinsing for direct comparison. Most hot spots on the untreated sample disappeared after rinsing, leaving only a few for each image covering an area of 35×55 micrometers squared. The rinsed sample pretreated with ionic liquid retained most hot spots on the Raman image. To confirm the removal of nanoparticles after rinsing, SEM images were collected from the same areas from both samples. The SEM images show that most nanoparticles were removed after rinsing from the untreated sample, while a high density of gold nanoparticles remained on the pretreated sample. On the rinsed untreated sample, the nanoparticles were mostly isolated. A few aggregates are observed and their size was typically below five nanoparticles for an aggregate. The largest aggregate included a dozen nanoparticles. For the rinsed sample treated previously with ionic liquid, the nanoparticles were rarely isolated. They tended to form larger aggregates. Most aggregates contained 10 to 30 nanoparticles. Most nanoparticles and aggregates of nanoparticles observed by SEM yielded a hot spot with variable enhancement on their corresponding Raman images, especially for the pretreated sample with the largest aggregates. For the untreated sample with the smaller aggregates, a large number of isolated nanoparticles and small aggregates yield no hot spot on the Raman image. The larger aggregate size in the pretreated sample explains the higher intensity of the hot spots, as aggregate size affects the appearance of hot spots and the nanoparticle surface plasmon resonance. Similarly, the intensity decrease of all hot spots in the pretreated sample after rinsing can be explained by a reduction in aggregate size. This intensity decrease might also be due to removal of some ionic liquid during the rinsing. Overall, the Raman and SEM images showed no preferential deposition of nanoparticles in the cell corners, middle lamella, or secondary cell walls.

After the second series of Raman images, but before the acquisition of SEM images, a series of Raman images at different depths from −4 to +6 micrometers were acquired for the untreated and pretreated samples. A depth of 0 corresponds to the surface of the sample. At this depth, the optical image of the sample is focused and the instrument was aligned so that the Raman intensity from dry wood is maximal when the optical image is focused. Positive depths correspond to a shorter distance between the objective and the sample, meaning the laser line is focused inside the sample. The cell walls aligned along the vertical direction of the images exhibit a consistently higher Raman intensity than those aligned along the horizontal direction. This is attributed to the incident laser being naturally polarized along the vertical direction of the image and the orientation of the cellulose fibrils. The cellulose fibrils in the secondary wall layer, closer to the lumen and generally the thickest, were found to be aligned along the grain of the wood, while those of the secondary wall closest to the middle lamella form an angle greater than 45 degrees with the direction along the grain of the wood. The intensity of all hot spots varied as the depth was changed. Most hot spots in the pretreated sample were still visible in the image collected at a depth of 6 micrometers, while only a few were visible at the same depth in the untreated sample. The laser line focusing enabled the collection of Raman images at a reasonable exposure time of less than 30 minutes for each image, and also an accurate registry.

To determine whether the gold nanoparticles were adsorbed at the sample surface or incorporated inside the sample, the intensity of six and twelve hot spots was measured as a function of depth for the untreated sample and pretreated sample, respectively. Included were all hot spots that could be tracked across the images at different depths. A few hot spots were excluded because their intensity depth profiles exhibit two distinct maxima. A few large aggregates contained nanoparticles stacked on top of others, and so it was unclear if the maxima correspond to hot spots from the same nanoparticles or multiple nanoparticles. The intensity depth profiles have full width at half maximum ranging from 2 micrometers for the most intense hot spots to 4 micrometers for the less intense hot spots. The depth resolution was sufficient to determine whether the particle is at the surface or incorporated inside the sample.

For the untreated sample, the intensity of hot spots reached a maximum at depth of approximately 0 micrometers or at a negative depth. The area under the curve for all depth profiles is dominated by contributions from negative depths. The electromagnetic field enhancement around the nanoparticles leading to SERS activity is local, only noticeable within a distance of 10 nm from the nanoparticles. Therefore, the nanoparticles producing these hot spots are all at the surface of the sample. As for the pretreated sample, we examined the intensity depth profiles of six hot spots from nanoparticles at the surface and six others from nanoparticles incorporated inside the sample. At least two hot spots reach their maximum intensity at a depth of 4 micrometers. This depth is 40 times the diameter of the nanoparticle. We estimate that at least 25 percent of the nanoparticles were below the surface.

The incorporation of nanoparticles in the pretreated sample is attributed to the expansion of wood cells upon exposure to the ionic liquid. Without wishing to be bound by any particular theory or explanation, the expansion and disruption of hydrogen bonding in the wood increased the distance between polymer chains inside the wood structure, paving the way for the incorporation of nanoparticles. The contraction of the cell walls after rinsing made it likely that the nanoparticles would remain in the sample even after rinsing. As for the untreated sample, water tends to adsorb on cellulose and hemicellulose by forming hydrogen bonds. The more limited expansion of untreated wood samples and the formation of hydrogen bonds between water and wood cells restrict the access of nanoparticles inside the sample. The nanoparticles at the surface of the untreated sample are only weakly adsorbed and can be easily washed away by rinsing.

Most reports on the dissolution of wood in ionic liquids have been conducted at temperatures typically above 90° C. U.S. Pat. No. 7,674,608, issued Mar. 8, 2010, for example, describes dissolving wood in ionic liquid at elevated (100-50° C.) temperatures. Development of alternative pretreatments at room temperature is desirable to reduce the cost of processing lignocellulosic biomass into fuel and other chemicals. The pretreated wood and method for preparing the pretreated wood of this invention provides a solution to this problem because the pretreated wood can be subjected to steps that advance the process of transforming the biomass into fuels and other chemicals.

The method of this invention may be applied at room temperature, providing a large cost savings in processing lignocellulosic biomass into fuel and other chemicals. The method of this invention may be applied in a temperature range from about 10° C. to about 50° C. Room temperature (approximately 25° C.) is preferable because the sample need not be heated or cooled.

The incorporation of metallic nanoparticles into wood at room temperature could be used as a cost effective method for reducing the crystallinity of wood by the delivery of particles in the wood structure at room temperature, removing and recycling the ionic liquid by replacing it with a co-solvent such as water or alcohol, and then subjecting the wood to microwaves. Microwaves are among the least expensive forms of energy amongst electromagnetic radiation to deliver electromagnetic radiation to a substance. Microwaves also have an ability to penetrate deeply within a large sample of a material. The microwaves may induce dielectric breakdown among the nanoparticles in the wood. The arcing between the particles creates damage to the cell wall structure and may provide a cost effective method to create sites of attack for enzymes and/or other chemicals for breaking down the lignocellulosic biomass.

Once the cell wall structures are damaged, the nanoparticles may be separated and reused. Some examples of techniques useful for separating these nanoparticles include, but are not limited to, including filtration and centrifugation. Magnetic separation is also possible when the metal nanoparticle used with the invention includes, for example, an electrically conductive shell and a magnetic core.

In U.S. Provisional Patent Application Ser. No. 61/326,121 entitled "Pretreated Wood Article and Method," filed Apr. 20, 2011, incorporated by reference herein, a process that involves the expansion and contraction of wood in ionic liquid at room temperature was developed to incorporate metal nanoparticles of 100 nm diameter at depths up to 4 μm into the wood structure. This work was subsequently published [22, 25]. The combination of incorporation of these nanoparticles followed by exposure to microwaves is believed to improve access of enzymes to cellulose. The ionic liquid causes swelling of the wood to an extent that allows incorporation of metal nanoparticles into the wood, which is subsequently treated with microwaves.

This incorporation process involving ionic liquids was used to incorporate various metallic and metallic oxides nanoparticles into the wood structure at room temperature. Among the selected metals, Fe was proven to be an excellent microwave absorber [23, 24] that can convert microwave irradiation into heat transferable to the surrounding wood structure. The evolution of the structure of poplar sections after microwave irradiation was monitored by optical microscopy for samples pretreated with ionic liquid 1-ethyl-3-methyl-imidazolium acetate (EMIMAc) with or without embedded metallic and metallic oxides nanoparticles.

The ionic liquid is needed during the pretreatment and the incorporation of nanoparticles at room temperature. The ionic liquid could be separated from the nanoparticle-incorporated wood by a simple filtration.

Only minimal biomass dissolution occurs at room temperature with ionic liquids. Therefore, the purification of the ionic liquid during recycling is not required. This, coupled with the smaller amounts of ionic liquid used, could significantly reduce operation costs.

Concentrated suspensions of $Fe_2O_3$, $Fe_3O_4$, Fe and Cu nanoparticles were prepared by immersing 100 mg of nanopowder in 1 mL of deionized water without any surfactant in an argon atmosphere. Dilute suspensions were also prepared with a concentration 10 times lower. All suspensions were agitated with a vortex mixer just before their deposition of poplar samples. Pretreated poplar samples were first immersed in EMIMAc for 3 hours before the nanoparticle incorporation [22]. After the pretreatment, the excess EMIMAc was blotted with a KIM WIPE. One sample was then immersed in 40 μL of concentrated suspension and three others in 20 μL of dilute suspension. A second set of four samples was prepared without the EMIMAc pretreatment. A third set of three samples was only pretreated with EMIMAc for 3 hours. A fourth set of three samples was pretreated with EMIMAc and then rinsed with deionized water. A fifth set of three samples was simply rinsed with deionized water. The samples were left to dry for 1 hour in air before microwave irradiation.

In addition, 500 mg of poplar sawdust was placed in each of three test tubes. Two of the three samples were immersed in 2 mL of EMIMAc for 3 hours. After the EMIMAc pretreatment, most of the EMIMAc was blotted by pressing the sawdust between sheets of KIM WIPE. The sawdust was then transferred to two different test tubes. Three mL of diluted Fe suspension was added to the untreated sample and one of the pretreated sample. In the other pretreated sample, 3 mL of deionized water was added. The test tubes were vortex mixed at each preparation step.

The pretreated wood sections were placed on a glass slide. A commercial microwave oven (SHARP Carousel R-230K) was used to heat the wood samples. It was operated at the maximum power of 800 W at 2.45 GHz.

Optical images were collected from the samples treated with Fe nanopowder using a LEXT OLS4000 measuring laser confocal microscope (Olympus America Inc., Center Valley, Pa.) equipped with a 20× and a 50× objective. The microscope operates with a 405 nm excitation laser. Optical images at different magnifications with spatial coordinates from the microscope stage ensured that the same areas were imaged before the nanoparticle deposition and after microwave irradiation.

Nanoparticles of Fe, Cu, $Fe_2O_3$, and $Fe_3O_4$ were incorporated into the poplar cell structure after a pretreatment with EMIMAc. When droplets of concentrated suspension of nanoparticles were deposited, the water evaporated within 30 min, leaving a thick layer of nanoparticles on top of the sample. Instead, the dilute suspension led to an incomplete coverage of the sample by the nanoparticles and only a slight change in sample color. The samples were heated with a microwave oven for 3 min in the case of the concentrated suspension and for 3, 5 and 10 min in the case of the dilute suspension. The samples were placed on a glass slide at approximately the same location inside the oven to avoid significant variations in temperature.

The samples incorporated with nanoparticles of Cu, $Fe_2O_3$, and $Fe_3O_4$ appeared undamaged after microwave irradiation even after 10 min irradiation for samples prepared with the concentrated suspension. The samples curled when residual water evaporated, but no significant damage was observed after irradiation. Only a slight change in color was observed with a few of the Cu samples due to the oxidation of the nanoparticles. Similar experiments with suspensions of Au and Ag nanoparticles produced a localized cell wall structure modification.

As for the samples incorporated with Fe nanoparticles, the one prepared with the concentrated suspension was vaporized after 3 min irradiation. The layer of nanoparticles immediately above the sample turned from black to brown, indicating Fe oxidation. The nanoparticles around the original wood section remained black. No wood section was found under the layer of nanoparticles. Occasionally, samples which were submitted to the same pretreatment and 3 min irradiation would leave a brittle and charred fibrous residue.

For samples prepared with the dilute suspension, no macroscopic change was observed after 3 min irradiation. The samples turned from light yellow (original color of poplar) to brown after 5 min. irradiation and dark brown/black after 10 min.

Samples prepared without EMIMAc pretreatment were also exposed to the concentrated and dilute Fe nanoparticle suspension, and heated for the same duration. The sample prepared with the concentrated suspension was also vaporized after 3 min irradiation, with the nanoparticles immediately above it oxidized. No noticeable change in morphology and color was observed for the samples prepared from the dilute suspension. Only after 10 min irradiation did they turn from light yellow to light brown. The slight color change after 10 min is similar to the one observed in samples rinsed with deionized water only. Microscopically, the wood cell structure seemed intact after irradiation.

To investigate the origin of the color change observed in pretreated samples incorporated with Fe nanoparticles, one set of three samples was heated after EMIMAc pretreatment and another set after EMIMAc pretreatment and water rinsing. With or without water rinsing, the wood sections turned brown after 5 min irradiation and then black after 10 min. It was noted that the rinsed sample heated for 5 mM had one half with a lighter color. This is explained by the local presence of residual water which limited wood heating, since more energy is required to vaporize the water [17, 18].

Similar microwave experiments were performed on untreated and pretreated poplar sawdust. Three samples were prepared. The first was a mixture of untreated sawdust and Fe nanoparticles in water, the second was pretreated with EMIMAc then immersed in water, and the third was pretreated with EMIMAc and incorporated with Fe nanoparticles in water. All three samples were exposed to three microwave pulses of 10 s. After microwave irradiation, no change in color or boiling was observed in the first sample, despite a moderate rise in temperature, which is consistent with the results from the poplar section. In the second sample, pretreated without nanoparticles, most of the water was evaporated after vigorous boiling, leaving most sawdust on the tube walls. No significant color change was observed after three pulses of 10 seconds (s). As for the third sample, pretreated and incorporated with Fe nanoparticles, most of the water was also evaporated after vigorous boiling. The sawdust turned black after the first pulse of 10 s before complete water evaporation, with the test tube significantly hotter than the other two. These results confirm the efficient microwave absorption and heat transfer of Fe nanoparticles embedded into the wood structure with the EMIMAc pretreatment. The heating of the incorporated sample was more efficient with water as an additional microwave absorber than without water, reducing the irradiation time required for a color change from 10 min to less than 10 s. The charring of the pretreated section was quicker without nanoparticles than with nanoparticles. In contrast, for the sawdust immersed in water, charring was quicker with nanoparticles. This can be explained by a size dependence of the biomass and the enhancement of heat transfer to the finer sawdust with increased active surface area.

The sample pretreated with EMIMAc with Fe nanoparticles were examined microscopically after 10 min irradiation. The Fe nanoparticles formed aggregates of sizes ranging from less than a micron to a few tens of microns. The density of particles was mostly uniform across the incorporated sample. Most particles turned red after irradiation, indicating oxidation. The sample with Fe nanoparticles was found after microwave irradiation with the poplar secondary cell walls significantly swollen. The swelling is reminiscent of the swelling observed during EMIMAc pretreatment before water rinsing [22, 25], suggesting the presence of residual EMIMAc in the wood sample after rinsing. During swelling, the middle lamellae between cells remained smooth and straight [22]. Microscopic and spectroscopic signatures of EMIMAc disappeared when an anti-solvent, such as water, was added to the sample [22, 25]. The swelling observed after microwave irradiation indicates the evaporation of residual water in the sample. In contrast to the EMIMAc-treated samples, the irradiated sample with Fe nanoparticles exhibited irregular middle lamellae with the secondary cell wall detached from the middle lamella in a few cells. Others completely collapsed with their lumen closed.

The swelling of the secondary cell walls was non-uniform across the sample, with a few areas where the cell wall thickness remained fairly constant. This non-uniform swelling is consistent with the non-uniform change in sample color after 5 mM irradiation. This non-uniformity is explained by the curling of the sample while it is heated. The water evaporation rate in areas that became detached from the supporting glass slide is different from the one in areas that remained adsorbed on glass. Even with the swelling of the secondary cell walls, the dimensions of the sample decreased after irradiation.

Cell walls in the samples pretreated with EMIMAc without Fe nanoparticles presented noticeably different morphology. The cell walls became significantly thinner after irradiation and seemed almost reduced to the middle lamella. The sample treated with only EMIMAc was torn along the ray cells. An amorphous film covered most of it, but is thin enough to distinguish the outline of the underlying wood structure. Ionic liquids, such as EMIMAc, are known to be effective solvents for biomass at high temperatures [5]. The film could be partially dissolved poplar in residual EMIMAc. Images suggest that EMIMAc dissolves preferentially the cellulose-rich secondary cell wall. A previous fluorescence microscopy study indicated that EMIMAc interacted preferentially with the secondary cell wall starting with the layer closest to the lumen [22]. A similar amorphous film also covered the rinsed sample to a lesser extent and was mostly limited to the ray cells. This less advanced decomposition stage is attributed to the presence of residual water that delays the cell wall dissolution in EMIMAc.

The oxidation of Fe nanoparticles accompanied by the wood structure modifications and water evaporation confirm that Fe nanoparticles are effective microwave absorbers. A previous study showed that Fe microparticles (<40 µm) can be heated up to almost 200° C. after 60 s microwave irradiation in a comparable commercial oven [23]. Most studies on the dissolution of biomass in ionic liquids were conducted between 70° C. and 140° C. for several hours [5, 7, 8, 9, 10, 11, 12, 13, 18, 26]. The sample charring after 10 min irradiation and quick decomposition of the wood cell walls with ionic liquids only suggest that the actual temperature is much higher. Indeed, thermogravimetric analyses of imidazolium-based ionic liquids indicated that the onset of thermal degradation usually occurs at temperatures above 300° C. [27]. Similar analyses of cellulose (Avicel) [28], milled wood lignin [29] and various feedstocks, such as eucalyptus [30], sugar cane bagasse [28], and poplar [31], showed the onset of decomposition occurring at temperatures above 250° C. in air. The hemicellulose is assumed to degrade first, followed by cellulose, at temperatures ranging from 250-350° C. The lignin degrades at higher temperatures above 350° C. [30]. The generation of char is expected to produce even higher temperatures very quickly, since char is an excellent microwave absorber and is commonly used as an additive to promote pyrolysis [17].

Whereas the cell walls in the samples without Fe nanoparticles became significantly thinner, those with Fe nanoparticles embedded remained as wide or became wider after microwave irradiation. The irregular shapes of the middle lamellae after heating are in sharp contrast with the smooth and straight middle lamellae observed during the cell wall swelling with EMIMAc at room temperature [22]. These observations suggest that the presence of Fe nanoparticles localize the microwave heating of wood. The fact that the deposition of Fe nanoparticles at the surface of the sample resulted in no significant structure modification or color change even after 10 min suggests that incorporating the cell walls with the metal nanoparticles after EMIMAc pretreatment is essential to the efficient localized heat transfer to the wood. This is explained partially by the thermal conductivity of metallic Fe [32] that is two orders of magnitude higher than the one of $Fe_2O_3$ [33], wood [34] and a variety of imidazolium-based ionic liquids [35, 36].

The quick charring of the wood with EMIMAc pretreatment and without Fe nanoparticles, accompanied by the quick thinning of the poplar cell walls also may indicate that a significant amount of cellulose is lost in the form of water, volatiles and $CO_2$ during the microwave heating [37, 38]. No noticeable liquid product was found on the underlying glass slide after microwave irradiation. The amount of sugars lost is difficult to measure due to an unknown amount of residual EMIMAc in the pretreated wood. The irradiation time for the poplar sections was longer than those reported in the literature, from multiple pulses of a few seconds [6, 18] to 2 min [4]. However, in these previous studies, the samples (pulp or small chips) were completely immersed in ionic liquids. In the present work, most EMIMAc was blotted after pretreatment, reducing considerably the amount of EMIMAc required for delignification. In an up-scaled process, the ionic liquid could be simply separated from the pretreated biomass by mechanical filtration. Since the pretreatment is performed at room temperature (approximately 25° C.), little biomass is dissolved in EMIMAc. Therefore, the ionic liquid requires no purification step before the next pretreatment cycle, reducing the amount of water required in the process. The smaller amount of EMIMAc required coupled with the absence of purification between cycles would significantly reduce the operation costs [21].

Metallic and metallic oxide nanoparticles were incorporated into poplar using a pretreatment that expanded and contracted the wood cell wall structure. Fe nanoparticles were found to be the most efficient microwave absorbers that can disrupt the integrity of the lignocellulosic matrix within 10 min. A microscopic study of the wood structure after microwave irradiation showed the efficient localized heating of the sample. Control experiments without Fe nanoparticles led to a significant thinning of the cellulose-rich secondary cell walls and suggest significant losses of cellulose in the form of water, volatiles and $CO_2$. Since the ionic liquid is only needed during the incorporation process at room temperature, the ionic liquid contains little dissolved biomass and could be recycled by simple mechanical filtration. The smaller amounts of ionic liquid required, combined with the absence of an ionic liquid purification step, a lower energy and water use, would significantly reduce operation costs in an up-scaled pretreatment process.

The present invention is more particularly described in the embodiments above, which are intended as illustrative only, since numerous modifications and variations will be apparent to those skilled in the art. The invention may be applicable for incorporating materials/chemicals into wood and paper products, enabling isotope tracing, development of new pretreatments, sensing and imaging capabilities.

REFERENCES

The following references are incorporated by reference herein.

(1) Sims et al., "An Overview of Second Generation Biofuels Technology," *Bioresour. Technol.* 2010, vol. 101, pp. 1570-1580.

(2) Banerjee et al., "Commercializing Lignocellulosic Bioethanol: Technology Bottlenecks and Possible Remedies," *Biofuels, Bioprod, Biorefin.* 2010, vol. 4, pp. 77-93.

(3) Huber et al., "Synthesis of Transportation Fuels from Biomass: Chemistry, Catalysts, and Engineering," *Chem. Rev.* 2006, vol. 106, pp. 4044-4098.

(4) Mang et al., "Microwave-assisted Conversion of Lignocellulosic Biomass into Furans in ionic Liquid," *Bioresour. Technol.* 2010, vol. 101, pp. 1111-1114, available online Oct. 1, 2009.

(5) Zakrzewska et Ed., "Ionic Liquid-Mediated Formation of 5-Hydroxymethylfurfural—A Promising Biomass-Derived Building Block," *Chem. Rev. January* 2011, vol. 111, pp. 397-417.

(6) Sun et al. "Complete dissolution and partial delignification of wood in the ionic liquid 1-ethyl-3-methylimidazolium acetate," *Green Chem.* 2009, 11, 646-655.

(7) Fort et al., "Can ionic liquids dissolve wood? Processing and analysis of lignocellulosic materials with 1-n-butyl-3-methylimidazolium chloride," *Green Chem.* 2007, 9, 63-69.

(8) Kilpeläinen et al., "Dissolution of Wood in Ionic Liquids," *J. Agric. Food Chem.* 2007, 55, 9142-9148.

(9) Xie et al., "Thorough Chemical Modification of Wood-Based Lignocellulosic Materials in Ionic Liquids," *Biomacromolecules* 2007, 8, 3740-3748.

(10) Zavrel et al., "High-throughput screening for ionic liquids dissolving lignocellulose," *Bioresour. Technol.* 2009, 100, 2580-2587.

(11) Lee et al., "Ionic liquid-mediated selective extraction of lignin from wood leaching to enhanced enzymatic cellulose hydrolysis," *Biotechnol. Bioeng.* 2009, 102, 1368-1376.

(12) Singh et al, "Visualization of biomass solubilization and cellulose regeneration during ionic liquid pretreatment of switchgrass," *Biotechnol. Bioeng.* 2009, 104, 68-75.

(13) Bose et al., "Enzyme-Catalyzed Hydrolysis of Cellulose in Ionic Liquids: A Green Approach to the Production of Biofuels," *J. Phys. Chem. B* 2010, 114, 8221-8227.

(14) Pottkämper et al., "Applying metagenomics for the identification of bacterial cellulases that are stable in ionic liquids," *Green Chem.* 2009, 11, 957-965.

(15) Datta et al., "Ionic liquid tolerant hyperthermophilic cellulases for biomass pretreatment and hydrolysis," *Green Chem.* 2010, 12, 338-345.

(16) Kappe et al., "Controlled Microwave Heating in Modern Organic Synthesis," *Angew. Chem. Int Ed.* 2004, 43, 6250-6284.

(17) Robinson et al., "Microwave Pyrolysis of Wood Pellets," *Ind. Eng. Chem. Res.* 2010, 99, 459-463.

(18) Swatloski et al., "Dissolution of Cellulose with Ionic Liquids," *J. Am. Chem. Soc.* 2002, 124, 4974-4975.

(19) Kržan et al., "Microwave heating in wood liquification," *J. Appl. Polym. Sci.* 2006, 101, 1051-1056.

(20) Gabriel et al., "Dielectric parameters relevant to microwave dielectric heating," *Chem. Soc. Rev.* 1998, 27, 213-223.

(21) Stark, A. "Ionic liquids in the biorefinery: a critical assessment of their potential," *Energy Environ, Set.* 2011, 4, 19-32.

(22) Lucas et al., "Ionic Liquid Pretreatment of Poplar Wood at Room Temperature: Swelling and Incorporation of Nanoparticles," *ACS Appl. Mater. Interfaces* 2010, 2, 2198-2205

(23) Buchelnikov et al., "Heating of metallic powders by microwaves: experiment and theory," *J. Appl. Phys.* 2008, 104, 113505.

(24) Liu et al., "Enhanced electromagnetic wave absorption properties of Fe Nanowires in gigahertz range," *Appl. Phys. Lett.* 2007, 91, 093101.

(25) Lucas et al., "Reversible swelling of the cell wall of poplar biomass by ionic liquid at room temperature," *Bioresour. Technol.* 2011, 102, 4518-4523.

(26) Pinkert et al., "Ionic Liquids and their Interaction with Cellulose," *Chem. Rev.* 2009, 109, 6712-6728.

(27) Fox et al., "Flammability, thermal stability, and phase change characteristics of several trialkylimidazolium salts," *Green Chem.* 2003, 5, 724-727.

(28) Varhegyi et al., "Kinetics of the thermal decomposition of cellulose, hemicellulose, and sugarcane bagasse," *Energy & Fuels* 1989, 3, 329-335.

(29) Faix et al., "Study on low mass thermal degradation products of milled wood lignins by thermogravimetry-mass-spectrometry," *Wood Sci. Technol.* 1988, 22, 323-334.

(30) Barneto et al., "Thermogravimetric measurement of amorphous cellulose content in flax fibre and flax pulp," *Cellulose* 2011, 18, 17-31.

(31) Mészáros et al, "Thermogravimetric and Reaction Kinetic Analysis of Biomass Samples from an Energy Plantation," *Energy & Fuels* 2004, 18, 497-507.

(32) Fulkerson et al., "Comparison of the Thermal Conductivity, Electrical Resistivity, and Seeback Coefficient of a High-Purity Iron and an Armco Iron to 1000° C.," *J Appl. Phys.* 1966, 37, 2639-2653.

(33) Shinde et al., "Investigation of structural, morphological, luminescent and thermal properties of combusted aluminum-based iron oxide," *J. Solid State Chem.* 2010, 183, 2886-2894.

(34) Suleiman et al., "Thermal conductivity and diffusivity of wood," *Wood Sci. Technol,* 1999, 33, 465-473.

(35) Ge et al., "Thermal Conductivities of Ionic Liquids over the Temperature Range from 293K to 353K," *J. Chem. Eng. Data* 2007, 52, 1819-1823.

(36) Van Valkenburg et al, "Thermochemistry of ionic liquid heat-transfer fluids," *Thermochim. Acta* 2005, 425, 181-188.

(37) Jones et al., "Molecular Analysis of Primary Vapor and Char Products during Stepwise Pyrolysis of Poplar Biomass," *Energy & Fuels* 2010, 24, 5199-5209.

(38) Demirbas et al., "Products from Lignocellulosic Materials via Degradation Processes," *Energy Sources, Part A* 2008, 30, 27-37.

What is claimed is:

1. An article comprising:
    a wood substrate,
    nanoparticles deposited in cell walls in the wood substrate, wherein the nanoparticles comprise an elemental metal or metal oxide, and
    an ionic liquid in the wood, the ionic liquid being a molten salt comprised of 1 ethyl-3-methyl-imidazolium having a melting temperature less than or equal to 100° C.

2. The article of claim 1, wherein the elemental metal or metal oxide comprises iron, tin, cobalt, titanium, niobium, tantalum, chromium, molybdenum, tungsten, nickel, copper, gold, silver, alloys thereof, mixtures thereof, or oxides thereof.

3. The article of claim 1, wherein the elemental metal or metal oxide comprises iron.

4. An article comprising:
    a wood substrate,
    nanoparticles deposited in cell walls in the wood substrate, wherein the nanoparticles comprise an elemental metal or metal oxide, and
    an ionic liquid in the wood, the ionic liquid being a molten salt comprised of 1 ethyl-3-methyl-imidazolium acetate having a melting temperature less than or equal to 100° C.

5. The article of claim 4, wherein the elemental metal or metal oxide comprises iron, tin, cobalt, titanium, niobium, tantalum, chromium, molybdenum, tungsten, nickel, copper, gold, silver, alloys thereof, mixtures thereof, or oxides thereof.

6. The article of claim 4, wherein the elemental metal or metal oxide comprises iron.

7. A method for treating a wood substrate, comprising:
    exposing a wood substrate having cell walls to an ionic liquid that is a molten salt that has a melting temperature at or below a temperature of 100° C. to induce swelling in the wood,
    exposing the swollen wood to an aqueous suspension of nanoparticles whereby at least some of the nanoparticles become deposited in the cell walls, wherein the nanoparticles comprise an elemental metal, and
    subjecting the wood and metal nanoparticles inside the wood to microwaves.

8. The method of claim 7, wherein the ionic liquid is molten at room temperature.

9. The method of claim 7, wherein the elemental metal is selected from iron, cobalt, titanium, niobium, tantalum, chromium, molybdenum, tungsten, nickel, copper, gold, silver, alloys thereof, and mixtures thereof.

10. The method of claim 7, wherein the elemental metal is iron.

11. The method of claim 7, wherein the step of exposing the wood to an ionic liquid occurs at room temperature.

12. A method for treating a wood substrate, comprising:
- exposing a wood substrate having cell walls to an ionic liquid that is a molten salt that has a melting temperature at or below a temperature of 100° C. to induce swelling in the wood, and thereafter
- exposing the swollen wood to an aqueous suspension of nanoparticles whereby at least some of the nanoparticles become deposited in the cell walls, wherein the nanoparticles comprise an elemental metal and the ionic liquid comprises imidazolium, and
- subjecting the wood and metal nanoparticles inside the wood to microwaves.

* * * * *